US00PP09356P

United States Patent [19]

Warner

[11] Patent Number: Plant 9,356

[45] Date of Patent: Nov. 7, 1995

[54] CLIMBING MINIATURE ROSE PLANT NAMED 'CHEWIZZ'

[76] Inventor: Chris Warner, Greenfields, Brockton, Newport, Shropshire, England, TF10 9EP

[21] Appl. No.: 315,780

[22] Filed: Sep. 30, 1994

[51] Int. Cl.[6] ..... A01H 5/00

[52] U.S. Cl. ..... Plt./4

[58] Field of Search ..... Plt./2, 4, 7.1, 10.1

[56] References Cited

U.S. PATENT DOCUMENTS

P.P. 9,013 12/1994 Warner ..... Plt./4

*Primary Examiner*—Howard J. Locker

[57] ABSTRACT

A new and almost continuously and profusely blooming rose plant, of the climbing miniature class, having conspicuous, open-faced flowers with petals gently rounded shape but having a minute point on the centerline; such petals of brilliant orange with yellow at their base; the flowers being pleasantly highlighted by their placement over a healthy and dense crop of rich red-toned new foliage and glossy green mature foliage on a tall upright vigorously growing, well branched plant.

1 Drawing Sheet

BACKGROUND OF THE INVENTION

The present invention relates to a new and distinct variety of rose plant of the climbing miniature rose class which was originated by me by crossing, as the seed parent, 'Irish Beauty'×(Galway Bay×Sutter's Gold (U.S. Plant Pat. No. 885)) seedling and as pollen parent the rose plant known as 'Anna Ford'. Upon recognition of the attributes of this plant within the progeny of the stated cross, it was elected for further testing and observation. Upon recognition that this plant was novel and expressed numerous superior and desirable traits as described below, the plant of this application was assigned an international recognition name of 'Chewizz'. This plant has been asexually reproduced by me or under my direction by cuttings and by budding in Washington County, Oreg. Such asexual reproduction has conclusively shown that all distinguishing characteristics of this plant come true to form, are firmly fixed, and are faithfully transmitted through succeeding propagations.

Specimens described below were grown in Washington County, Oreg.

SUMMARY OF THE INVENTION

The new plant of this invention contains a number of outstanding attributes in combination which set it apart from all other plants of the miniature rose market class. Such characteristics may be summarized as follows:

A new and conspicuously attractive flower having bright orange petals.

Petals of gently rounded shape of bright orange coloring with yellow showing at base of petals, having a small point at the center of the rounded apex of the margin.

Open faced flowers which open to a substantially flat form.

Flowers being pleasantly highlighted above lush, dense foliage which is healthy in appearance.

A tall plant which is highly remontant and blooms almost continuously and profusely.

Flowers formed singly or in sprays placed over a healthy and dense crop of red-brown new foliage and deep green mature foliage of an upright compact but vigorously growing, well branched plant.

DESCRIPTION OF THE DRAWING

The submitted photographic illustration shows typical foliage and blooms of the new cultivar in various stages of maturity.

BOTANICAL DESCRIPTION OF THE PLANT

The following is detailed description of my new variety, with color terminology in accordance with The Royal Horticultural Society Color Chart (RHSCC). The terminology used in color description herein refers to plate numbers in the aforementioned color chart. "135C" is plate 135C of The Royal Horticultural Society Color Chart.

Parentage:

*Seed parent.*—Irish Beauty×(Galway Bay×Sutter's Gold (U.S. Plant Pat. No. 885)) seedling.

*Pollen parent.*—Anna Ford.

Class: Climbing miniature.

The following observations are made of specimens grown out doors in Washington County, Oreg. during June.

FLOWER

Blooming habit: Nearly continuous, with blooms occurring both singly and in flushes.

A. Bud:

(1) *Size.*—About 1.25 cm long, pointed buds with no foliaceous appendages to the buds.

(2) *Form.*—Pointed.

(3) *Color.*—The reverse of petals is bright orange color (32A) with yellow base (16A).

(4) *Sepals.*—Permanent, spear shaped, reflexed color green (137A).

(5) *Peduncle.*—Length — about 4 cm. Aspect — straight. Strength — erect, but some arching. Color — near 137A green.

B. Bloom:

(1) *Size.*—When fully expanded — about 3.5 cm.

(2) *Borne.*—Singly and in sprays of 4 to 7 blooms.

(3) *Form.*—Flat, slightly cupped inward.

(4) *Petalage.*—About 10 under normal conditions.

(5) *Color.*—Bright orange (32A) on inner and outer sides of petals with yellow (16A) at the base. Petal aging causes orange to pale to (33C).

C. Petals:
(1) *Texture.*—Moderately thick and of good substance.
(2) *Appearance.*—Velvety, both inside and outside.
(3) *Form.*—The bloom has flat form with shallow depth. Petals stand at right angles to calyx. The petals are round.
(4) *Arrangement.*—Regularly arranged.
(5) *Petaloids in center.*—Medium, surrounding center.
(6) *Persistence.*—Petals drop off cleanly.
(7) *Fragrance.*—Spicy fragrance.
(8) *Lasting quality.*—Blooms last about five days cut or on the bush.

REPRODUCTIVE ORGANS

A. Stamens, filaments and anthers:
(1) *Arrangement.*—Regularly arranged stamens around low pistils.
(2) *Color.*—Medium yellow, aging to darker yellow.
B. Pollen:
*Color.*—Medium yellow.
C. Styles: Long, even length — introrse.
D. Stigmas:
*Color.*—Medium yellow.
E. Hips: About 1 cm.
F. Sepals: Permanent, spear shaped, reflexed.

PLANT

A. Form: Tall, upright.
B. Growth: Uniform branching to about 7 feet tall with good vigor. Pinching induces further branching.
C. Foliage: Compound 5 leaflets (most often).
(1) *Size.*—1½ cm leaflets.
(2) *Quantity.*—Abundant.
(3) *Color.*—New foliage red-toned 178A, changing to 137B green.
(4) *Shape.*—Oval, pointed.
(5) *Texture.*—Glossy.
(6) *Edge.*—Serrated.
(7) *Serration.*—Very Fine, saw-shaped.
(8) *Leaf stem.*—Color — green 135C.
(9) *Stipules.*—Lightly bearded, and ¾ cm long.
(10) *Rachis.*—Green color, medium 1 cm, upper side grooved.
(11) *Resistance to disease.*—Blackspot — Average. Mildew — Average. Rust — Average.
D. Wood:
(1) *New wood.*—Color — red-toned 178A turning light green 137B. Bark smooth.
(2) *Old wood.*—Color — green 136B, Bark — smooth with sturdy growth — 3 cm internodes.
E Thorns:
*Quantity.*—Both main stalk and laterals from stalk are average.
*Form.*—Dilated at base and declining.
*Length.*—⅓ cm.
*Color.*—Red-toned 178A changing to brown at maturity.
*Position.*—Ordinary.
*Prickles.*—Average.
F. Winter hardiness: Requires ordinary protection in in extreme climates.

I claim the following:

1. A new and distinct variety of climbing miniature rose plant substantially as described and illustrated, which is particularly characterized by being easy to propagate; vigorous, hardy, bushy and upright habit; having blooms borne singly or in sprays from 4 to 7 which open quickly to a flat form showing yellow stamens; as having petals of conspicuously bright orange with yellow at the base; and, the flowers being produced in abundance covering the lush red-toned and green foliage.

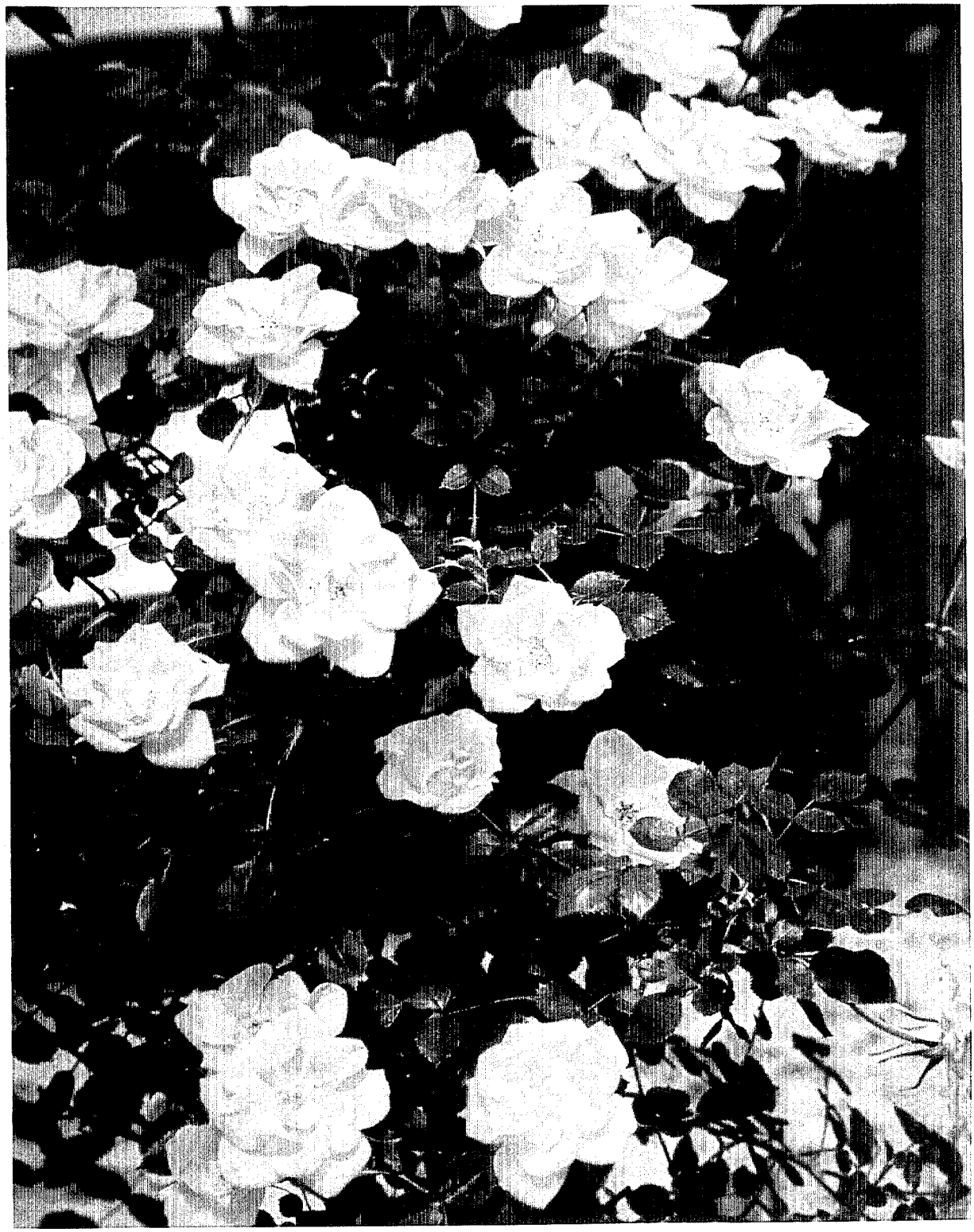

* * * * *